US008255238B2

(12) United States Patent  (10) Patent No.: US 8,255,238 B2
Powell et al.  (45) Date of Patent: Aug. 28, 2012

(54) SYSTEM AND METHOD FOR REAL TIME VIEWING OF CRITICAL PATIENT DATA ON MOBILE DEVICES

(75) Inventors: William Cameron Powell, San Antonio, TX (US); Trey Moore, San Antonio, TX (US)

(73) Assignee: AirStrip IP Holdings, LLC, San Antonio, TX (US)

( * ) Notice: Subject to any disclaimer, the term of this patent is extended or adjusted under 35 U.S.C. 154(b) by 1080 days.

(21) Appl. No.: 11/301,348

(22) Filed: Dec. 12, 2005

(65) Prior Publication Data

US 2006/0149597 A1 Jul. 6, 2006

Related U.S. Application Data

(60) Provisional application No. 60/641,057, filed on Jan. 3, 2005.

(51) Int. Cl.
*G06Q 50/00* (2012.01)
*G06F 15/16* (2006.01)
*A61B 5/00* (2006.01)

(52) U.S. Cl. ............... 705/3; 705/2; 709/217; 600/300
(58) Field of Classification Search .............. 705/2–3; 709/217; 600/300
See application file for complete search history.

(56) References Cited

U.S. PATENT DOCUMENTS

| | | |
|---|---|---|
| 5,827,180 A | 10/1998 | Goodman |
| 5,954,663 A | 9/1999 | Gat |
| 5,987,519 A | 11/1999 | Peifer et al. |
| 6,093,146 A | 7/2000 | Filangeri |
| 6,168,563 B1 | 1/2001 | Brown |
| 6,272,469 B1 | 8/2001 | Koritzinsky et al. |
| 6,302,844 B1 | 10/2001 | Walker et al. |
| 6,336,900 B1 | 1/2002 | Alleckson et al. |
| 6,364,834 B1 | 4/2002 | Reuss et al. |
| 6,383,137 B1 | 5/2002 | Berry |

(Continued)

FOREIGN PATENT DOCUMENTS

CN 1270676 A 10/2000

(Continued)

OTHER PUBLICATIONS

First Examination Report for Application No. 2006213066, mailed Apr. 23, 2010, 2 pages.

(Continued)

*Primary Examiner* — Lena Najarian
*Assistant Examiner* — Minnah Seoh
(74) *Attorney, Agent, or Firm* — Fish & Richardson P.C.

(57) ABSTRACT

A data-processing tool for displaying real-time patient data on remote and/or mobile devices. The tool renders graphical data on the screen of the remote device in a manner that makes it practical for the health care provider to review the data. Charting components provide landscape support, an ability to overlay patient data and patient images, zoom in/zoom out, custom variable speed scrolling, split screen support, and formatting control. The methodology operates as an asynchronous application, allowing patient data to be streamed in real-time to the handheld device while conserving enough CPU power to simultaneously allow the end user to interact at will with the responsive display application. Finally, the methodology implements an IT management console that allows system managers to monitor the exchange of data between hospital systems and the primary database, including all patient data packets, notifications and alerts, connected remote devices, etc.

22 Claims, 14 Drawing Sheets

U.S. PATENT DOCUMENTS

| | | |
|---|---|---|
| 6,409,659 B1 | 6/2002 | Warner et al. |
| 6,416,471 B1 | 7/2002 | Kumar et al. |
| 6,475,146 B1 | 11/2002 | Frelburger et al. |
| 6,520,910 B1 | 2/2003 | Kohls |
| 6,523,009 B1 | 2/2003 | Wilkins |
| 6,587,829 B1 | 7/2003 | Camarda et al. |
| 6,589,170 B1 | 7/2003 | Flach et al. |
| 6,616,613 B1 | 9/2003 | Goodman |
| 6,641,533 B2 | 11/2003 | Causey, III et al. |
| 6,684,276 B2 | 1/2004 | Walker et al. |
| 7,038,588 B2 | 5/2006 | Boone et al. |
| 7,353,179 B2 | 4/2008 | Ott et al. |
| 2001/0044588 A1 | 11/2001 | Mault |
| 2002/0198473 A1* | 12/2002 | Kumar et al. .............. 600/595 |
| 2003/0078806 A1 | 4/2003 | Kudryk et al. |
| 2003/0085870 A1* | 5/2003 | Hinckley ..................... 345/156 |
| 2003/0115415 A1 | 6/2003 | Want et al. |
| 2003/0236682 A1 | 12/2003 | Heyer |
| 2005/0206518 A1 | 9/2005 | Welch et al. |

FOREIGN PATENT DOCUMENTS

| | | |
|---|---|---|
| JP | 2000316820 | 11/2000 |
| WO | WO9914882 A3 | 3/1999 |
| WO | WO2004084720 A3 | 3/2005 |

OTHER PUBLICATIONS

Second Examination Report for Application No. 2006213066, mailed Feb. 24, 2011, 2 pages.

Second Office Action for Application No. 200680006961.7, mailed Apr. 8, 2011, 5 pages.

Authorized officer Blaine R. Copenheaver, International Search Report and Written Opinion of the International Searching Authority for International Application No. PCT/US2010/026993, mailed May 11, 2010, 8 pages.

International Preliminary Report on Patentability (1 page) dated Jul. 3, 2007 and Written Opinion of the International Searching Authority (3 pages) dated Jun. 5, 2006 for International Application No. PCT/US2006/000035.

International Search Report for International Application No. PCT/US2006/000035, dated Jun. 5, 2006, 2 pages.

Supplementary European Search Report for Application No. 06717260.1, mailed Aug. 2, 2010, 7 pages.

Authorized Officer Philippe Bécamel, International Preliminary Report on Patentability for Application No. PCT/US2010/026993, dated Sep. 22, 2011, 6 pages.

First Office Action for Application No. 200680006961.7, mailed Nov. 2, 2010, 11 pages.

* cited by examiner

SYSTEM AND METHOD FOR REAL TIME VIEWING OF CRITICAL PATIENT DATA ON MOBILE DEVICES

CROSS REFERENCE TO CORRESPONDING APPLICATIONS

This application claims the benefit under Title 35 United States Code §119(e) of U.S. Provisional Application No. 60/641,057 filed Jan. 3, 2005.

BACKGROUND OF THE INVENTION

1. Field of the Invention

The present invention relates generally to systems and methods for transmitting, receiving and displaying information over wireless communication and data processing devices. The present invention relates more specifically to a system and method for collecting, uploading, transmitting, receiving, downloading, manipulating, and displaying medical patient data to a mobile display device operable by the patient's physician or health care provider.

2. Description of the Related Art

While physicians and other health care providers currently utilize a large number of products and systems that benefit from advances in wireless communication technology, there are still significant limitations to the information that can be transmitted, received, and displayed over these devices in a practical and efficient manner. While text messaging and voice communications have been fairly well established in the health care and medical fields, the wireless transmission of critical patient data has, for a number of reasons, been slow to develop. There are many limitations that are intrinsic to mobile devices, especially those constraints related to speed, performance, memory, and display size. In addition, because of the critical nature of the data, it is important that the technology work reliably and efficiently over potentially low speed, low bandwidth, and sometimes intermittent cell phone connections.

Efforts have been made in the past to transmit medical information through various telecommunication means to health care professionals for review and analysis. These efforts include the following:

U.S. Pat. No. 6,589,170 B1 issued to Flach et al. on Jul. 8, 2003, entitled *Medical Telemetry System with Cellular Reception of Patient Data*. In something of the reverse of the present invention, the Flach et al. disclosure describes a system that collects patient data by telemetry from wireless patient sensor units. The data is collected and concentrated in standard hospital network information processing systems.

U.S. Pat. No. 6,093,146 issued to Filangeri on Jul. 25, 2000, entitled *Physiological Monitoring*. Similar to Flach et al., this patent likewise describes a system whereby the patient data is wirelessly communicated to a nearby base station from which the data may then be transmitted (by wire line) to a remotely accessible telephone network.

U.S. Pat. No. 6,302,844 B1 issued to Walker et al. on Oct. 16, 2001, entitled *Patient Care Delivery System*. The system described in the Walker et al. patent identifies anomalies in colleted patient data and determines whether it is necessary to contact a physician (by telephone, for example) regarding the anomalous event.

U.S. Pat. No. 6,416,471 B1 issued to Kumar et al. on Jul. 9, 2002 entitled *Portable Remote Patient Telemonitoring System* describes yet another system for collecting patient data from a wireless sensor device on the patient and transmitting it to a nearby base station from which the information is sent by standard techniques to a remote monitoring station.

U.S. Pat. No. 6,336,900 B1 issued to Alleckson et al. on Jan. 8, 2002, entitled *Home Hub for Reporting Patient Health Parameters* provides for yet another system that collects patient data from wireless transmitting sensors on the patient and places the information/data on a public data transmission network.

U.S. Pat. No. 6,168,562 B1 issued to Brown on Jan. 2, 2001, entitled *Remote Health Monitoring and Maintenance System* describes a patient monitoring system that adds the capability of remotely re-programming the sensor system associated with the patient so as to alter the manner in which it collects patient data.

U.S. Pat. No. 6,475,146 B1 issued to Frelburger et al. on Nov. 5, 2002, entitled *Method and System for Using Personal Digital Assistants with Diagnostic Medical Ultrasound Systems*. The primary purpose of the system described in the Frelburger et al. disclosure is to permit the use of a PDA as a source of control information, data, and/or commands to carry out the operation of an ultrasound examination system.

U.S. Pat. No. 6,520,910 B1 issued to Kohls on Feb. 18, 2003, entitled Method and System of Encoding Physiological Data. This system focuses on the transfer of high-resolution data to workstations with lower-performance capabilities in order to permit some level of data analysis thereon. The patent describes the manipulation of graphic files for the purpose of making the high-resolution data more accessible.

U.S. Pat. No. 6,383,137 B1 issued to Berry on May 7, 2002, entitled *Labor Alerting Device*. This patent describes the use of an implanted monitor to detect the on-set of labor and to transmit a signal to a pager or PDA that notifies the patient or the patient's physician of the impending birth. The system does not communicate data beyond the simple event notification.

U.S. Pat. No. 6,616,613 B1 issued to Goodman on Sep. 9, 2003, entitled *Physiological Signal Monitoring System*. The Goodman patent describes a system specifically designed to communicate photoplethysmography (PPG) data from a patient to a system web server for analysis, storage and later retrieval. The patent is specific to the monitoring of the circulatory system and endeavors to analyze heart and blood data for remote monitoring.

U.S. Pat. No. 6,641,533 B2 issued to Causey, III et al. on Nov. 4, 2003, entitled *Handheld Personal Data Assistant (PDA) with a Medical Device and Method of Using the Same*. This patent describes the localized use of a PDA in conjunction with a medical device for the processing of data received there from. The system focuses on the ability to remotely program the medical device with the PDA and the snapshot presentation of data thereon.

U.S. Pat. No. 5,954,663 issued to Gat on Sep. 21, 1999, entitled *Fetal Monitoring System and Method* describes one system for the collection and storage of patient data that includes fetal heart rate and uterine contraction data. The patent addresses the integration of multiple monitoring systems within a hospital setting but does not discuss conditioning the data for transmission over wide area networks or wireless devices.

The above identified systems in the related art variously describe attempts to utilize wireless data communication technologies to transmit medical information to health care providers, or to condition data such that it may be useful for remote monitoring purposes. The ability to transmit real-time graphical data in a discernable form to small hand-held type devices is noticeably lacking from all of the systems described. While the collection of patient data and the wireless transmission of the same to some local hub has been quite thoroughly explored, such systems have no need to consider the ability to display such data in useful form on display systems with lower memory and processing capacities such as PDAs. At best the above systems anticipate the display of snapshots of data that in most circumstances is wholly insufficient to allow the physician to make a judgment about the condition of a patient or the proper course of action to take.

It would be desirable to provide a system that is capable of transmitting patient physiological data over a wide area data communications network with a resolution sufficient to provide real-time monitoring and accurate analysis by a remote physician or health care provider. It would be desirable if the system could communication more than a single physiological parameter and could display the same with a discernable resolution on a small display screen such as may be present on a PDA or cellular phone. It would be desirable if the system allowed the remote health care provider not only view the data in real-time but to also scroll backward through the data to identify and characterize trends in the patient's condition. It would be desirable if the display capabilities included features such as landscape/portrait viewing, patient biographical data viewing, patient image viewing, zoom in/out graphical data viewing, variable speed scrolling and HIPAA compliant information security measure. It would be desirable if such a system could be implemented using currently available operating systems for hand held data communication devices over currently available bandwidth on established wide area data and telecommunication network systems.

SUMMARY OF THE INVENTION

The development of the present invention stems from the growing realization of the benefits of viewing real time critical patient data on mobile devices, such as Pocket PC® handheld devices and other PDA or cellular phone devices, and further from realizing how the utilization of this capability can dramatically improve overall patient healthcare. The basic system and method of the present invention function particularly well with fetal heart and maternal monitoring data, but are capable of functioning in conjunction with more complex displays such as 12-lead EKG data in a manner similar in form and function. In general, the system and method of the present invention can be applied to the transmission, reception, and display of any type of wave form, rhythm, or "free form" data associated with the physiological condition of a patient.

The methodology of the present invention is made possible in part by recent developments in certain software platform technologies and the gradual movement to the use of smart client applications in small wireless devices. The present methodology is built on Microsoft's .NET® platform which is a software platform that connects information, users, systems, and devices, and provides a bridge between clients, servers, and developer tools. The Microsoft .NET® platform is currently being utilized to build and run various types of software, including web-based applications, smart client applications, and XML web services. "Web services" as used herein, are simply components that facilitate the sharing of data and functionality over a network through standard platform independent protocols such as XML, SOAP, and HTTP.

The methodology of the present invention incorporates software systems that are specifically designed for use in smart client applications. The term "smart client" highlights the differences between the typical "rich client" applications commonly utilized in the medical field, and the next generation of client applications. Smart client applications combine the benefits of a rich client model with the benefits of a thin client model, especially as they relate to mobility, manageability and functionality. Smart client applications also provide much more flexibility than the traditional rich client applications, and can be built to take maximum advantage of the features provided by the host device. In general, smart client applications display the following characteristics:

1. Smart client applications utilize local resources such as the local CPU or GPU, local memory or disk, or other local devices connected to the client such as a cellular modem, pager vibrator, etc. In addition, they take advantage of locally operable software including various Microsoft® applications such as Instant Messenger® and Pocket Outlook®.
2. Smart client applications may generally be referred to as connected in so far as they generally do not operate in a stand alone mode, and always form part of a larger distributed system. In this manner the smart client application may interact with a number of different web services that provide access to the common or shared application data.
3. Despite the connected operation described above, smart client applications are typically offline capable in that they run on the local machine and are able to function with data or information received even when the user is not immediately connected to a server. An example of this in the environment of the present invention may be seen where a doctor may be stepping into an elevator with no wireless connectivity available, or a building location where weak cell phone coverage exists even when the client is connected, the smart client application can improve performance and usability by caching data and managing the connection in an intelligent way.
4. Smart client applications generally operate with intelligent install and update features. In this way they manage their deployment, and update in a much more intelligent way than traditional rich client applications. The .NET framework enables application artifacts to be deployed using a variety of techniques, including simple file copy or download over HTTP. Applications may be updated while running, and can be deployed on demand by browsing to a specific URL. In addition, the Microsoft .NET® framework provides security mechanisms that insure the integrity of the application in its related assemblies. Assemblies can be given limited permissions in order to restrict their functionalities in semi-trusted situations.
5. Finally, smart client applications provide client device flexibility. The .NET framework together with the .NET compact framework provides a common platform upon which smart client applications can be built. Often there will be multiple versions of a smart client application, each targeting a specific device type, and taking advantage of the device's unique features to provide functionality appropriate to its usage. For example, a PDA phone can receive an SMS message for an alert coming from a central monitoring system at a hospital, or the application could be configured to cause the data phone to vibrate and/or generate an audible sound when a severe alert is detected and received. The platform on which the present invention is based is capable of taking advantage of all of these device specific features.

The system and methodology of the present invention take advantage of the above technologies and add to them significant customized charting components to provide a useful tool for the viewing of real-time critical patient data on mobile devices. Currently there are very few third party components on the market for PDAs that provide the appropriate functionality necessary for the operation of the present system and method.

The most important requirement to implement the system and method of the present invention is the ability to utilize as much screen "real estate" as possible in order to provide a visual graphic display that offers discernable data to the health care provider. Working against the clear display of high-resolution data are screen size and display memory capacities. The present invention optimizes the amount of information (patient data) that can be displayed in a discernable manner on the smaller screens of typical handheld devices.

In addition to optimizing the display, the efficiency with which a drawing, a figure or a data set is displayed on the screen is crucial because any processing time taken to create or draw an image on the screen is time taken away from data processing which significantly reduces the overall efficiency of the data communication. The present invention therefore seeks to optimize the image rendering process for handheld device displays.

To achieve these display related objectives, a customized charting control is established and implemented in the present invention using the latest GDI+ and PDA drawing techniques. These charting components provide a number of advantages over existing charting systems on the market, including landscape support, the ability to overlay patient data and patient images, zoom in/zoom out, custom variable speed scrolling, split screen support (for example it would not be possible to create the OB Strip without showing both fetal heart rate and maternal contraction simultaneously), and unlimited control over formatting (changing colors, font sizes, etc). In addition to GDI+, the present invention takes advantage of GAPI which stands for Game API (Application Program Interface), and is a set of protocols and tools that traditionally is only used for building game software. GAPI is appropriate for use with the present invention because it provides direct access to the video display memory of the devices running the applications, and thus allows for very high-performance and high quality graphic rendering. This not only allows for a better graphical display but also takes up significantly less CPU processing power which is then freed up for background processing tasks such as synchronizing data from the hospital to the PDA. GAPI is also supported on multiple PDA operating systems (Pocket PC®, Palm®, Symbiano, etc.).

In addition to the display related objectives discussed above, the present invention seeks to optimize interactive functionality and responsiveness for the remote physician or health care provider. Many different factors determine how fast network communication services may respond to an application making a request, including the nature of the request, network latency, reliability, the bandwidth of the connection, and how busy the service or services are. All of these factors can cause problems with the responsiveness of single threaded applications, and can ultimately result in dissatisfied end users who dislike the application (and eventually discontinue its use) due to its slow operation.

To achieve the responsiveness goals discussed above, the methodology of the present invention implements steps that utilize the benefits gained from an asynchronous application, without sacrificing the crucial processing time of the handheld device to handle user interface activity. In this manner, the methodology allows the critical patient data to be streamed in real-time to the handheld device in a background operation while it still conserves enough CPU power to simultaneously allow the end user to interact at will with the responsive applications (for example, looking for trends in the data by scrolling quickly back over a period of several minutes or hours).

The methodology of the present invention is structured using pure object oriented concepts and design patterns which allow it to achieve superior performance and scalability. Each logical tier of the methodology, from the data access objects to the charting control objects to the user interface objects, is structured with precise well defined interfaces that support enhancements and customization through both interface and implementation inheritance. In addition, the use of object models in advanced .NET programming language features such as reflection, delegates, and event handlers, allow the methodology to be customized for specific hospital implementation or for specific subject matter applications.

Finally, the methodology of the present invention implements an IT management console that allows system managers to monitor the exchange of data between hospital systems and the primary database, including (in the preferred embodiment) all fetal strip packets, notifications and alerts, connected remote devices, etc. In this manner, hospital technical support staff may as necessary, view the exchange of data and provide support and troubleshooting to its operation.

DETAILED DESCRIPTION OF THE PREFERRED EMBODIMENTS

Figure 1:
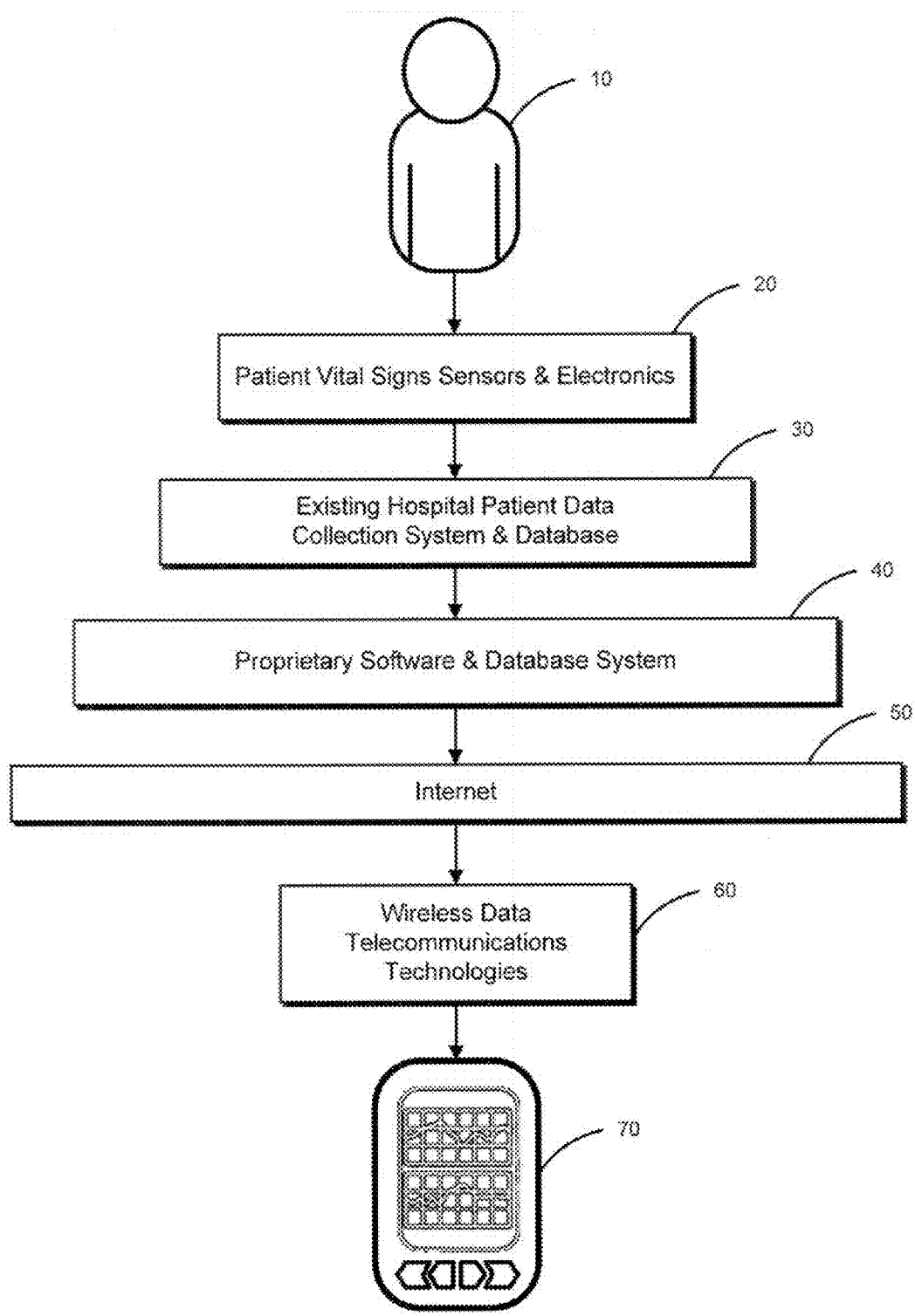
FIG. 1 is a high-level schematic block diagram showing the hardware and software structure for the complete system of the present invention.

Reference is made first to FIG. 1 for a summary overview of the existing and new components necessary for implementation of the system and methodology of the present invention. FIG. 1 is a top-level schematic block diagram showing the hardware and software structure for the entire system of the present invention from the patient 10 whose physiological data is being monitored to the handheld device 70 utilized by the physician doing the monitoring. Patient vital signs sensors and electronics 20 are used to derive the relevant patient physiological data in a manner well known in the art. A variety of known sensors and electronic monitoring devices have been developed capable of detecting physiological functions and converting sensed responses into analog and digital signals containing characteristic information regarding the patient's vital signs and health conditions.

Also known in the art are methods and systems which bring such patient information into the existing hospital patient data collection system and database 30. Such systems typically collect and store patient information (in the form of graphical data and the like) for the purpose of displaying such information at remote hardwired locations within the hospital or in some instances by telecommunication landlines to locations outside the hospital. The present invention introduces proprietary software and database system 40 which is, in part, the subject of the present application, into a data processing system integrated with or connected to the existing hospital systems 30. This software and database system 40 of the present invention takes the standardized graphical data associated with the monitored physiological events and prepares such data for its eventual display on remote wireless devices.

The Internet 50 provides the medium through which the configured and formatted data may ultimately be transmitted to the wireless remote devices to be displayed for the purpose of allowing a physician to remotely discern the information. From the Internet 50 standard wireless data telecommunication technologies 60 come into play to receive the configured information from the Internet 50 and provide it to a variety of different handheld devices 70 represented generically by a display on a PDA.

It is primarily the unique functionality of the proprietary software and database system 40 shown in the overall view of the entire system in FIG. 1 and the associated software present in the handheld device 60 that constitute the novel capabilities of the system of the present invention. While the present invention takes advantage of current technologies in both data communication and graphic displays it provides a heretofore unavailable manner of conveying multi-channel, real-time, quantified, graphical data to physicians at wireless remote display stations in the form of handheld devices.

Figure 2:
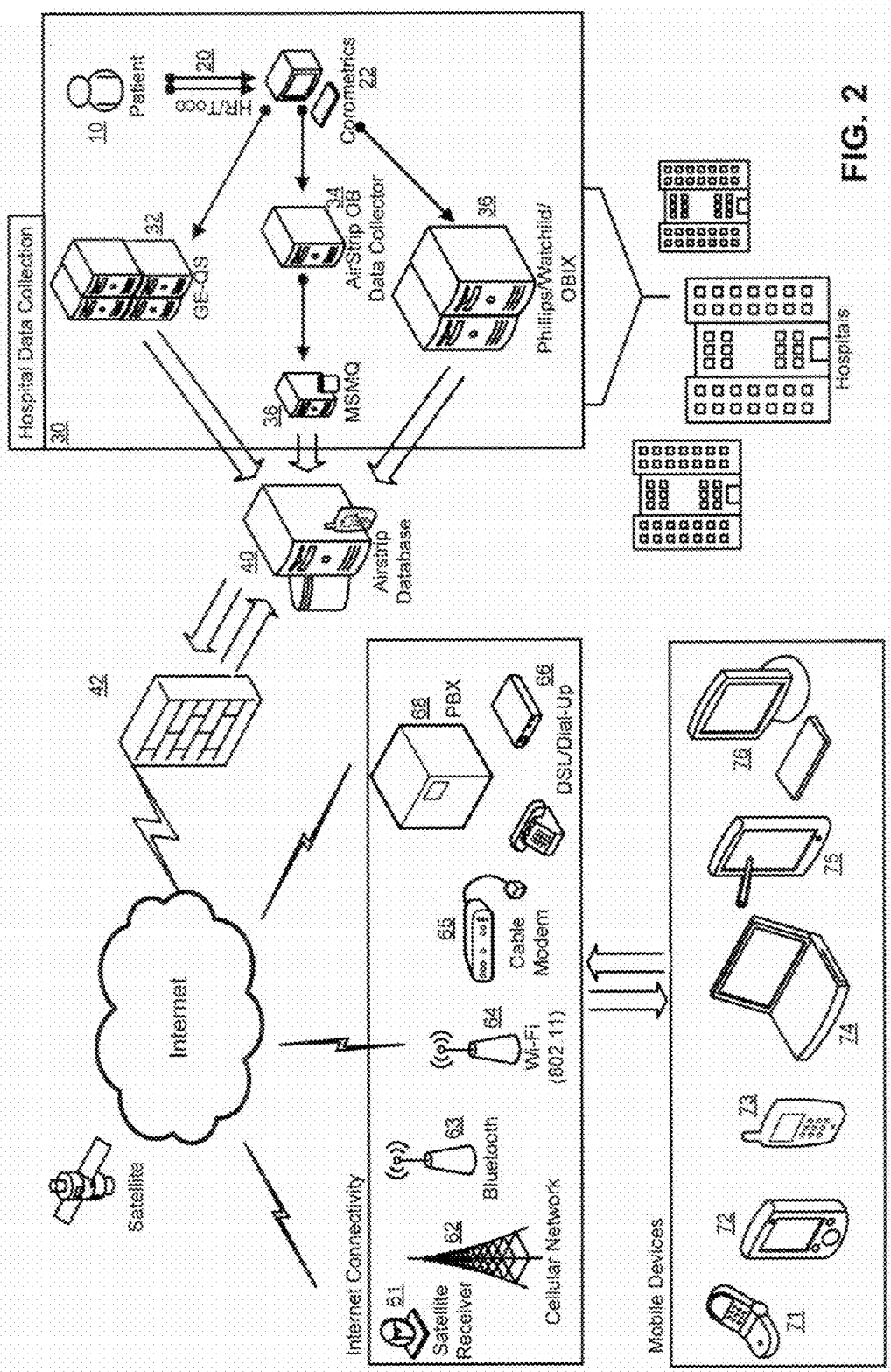
FIG. 2 is a mid-level schematic diagram of the data processing and communication components of the complete system of the present invention showing the various data communication paths, and providing an overview of the functionality of the system.

Reference is now made to FIG. 2 for a more detailed description of the hardware components associated with implementation of the system of the present invention to accomplish the task of communicating the necessary patient physiological characteristics required by the remote physician to carry out a decision with regard to patient condition. In the example of the present application, hospital 24 patient information is collected into the existing hospital patient data collection system and database systems 30 as shown in FIG. 2. In the present example, fetal heart rate and maternal contraction data 20 from patient 10 is gathered and passed through existing monitoring systems 22 known in the industry such as the Corometics Series Monitors offered by GE Healthcare. Existing clinical information systems, such as the GE QS Perinatal system 32, the Clinical Computer Systems, Inc. OBiX Perinatal Data system 36, the Hill-Rom Watch-Child system 36, and various similar obstetrics information systems by Philips Medical Systems, provide further processing and storage of the collected patient data. In addition the data is passed through the AirStrip OB Data Collector 34 of the present invention (described in more detail below) before being passed through Microsoft Message Queuing (MSMQ) 38 before finally being received and configured in the AirStrip Database System 40 of the present invention.

From AirStrip Database System 40 the data/information is provided through a web service/firewall 42 to the Internet 50. From the Internet 50 through a variety of Internet connectivity options 60 the information is eventually passed to the local mobile devices 70 retained by the remote physician. Internet connectivity 60 may be provided by means of satellite receiver 61, cellular network 62, Bluetooth system 63, Wi-Fi (802.11) system 64, cable modem 65, DSL/dial-up 66 and PBX system 68. Each of these Internet connectivity systems 60 may provide the data/information to the local devices 70 which may take the form of a smart phone 71, a PDA 72, a PDA phone 73, a Windows CE/.NET type device 74, Tablet PC type device 75, or a PC/Laptop type device 76.

Figure 3:
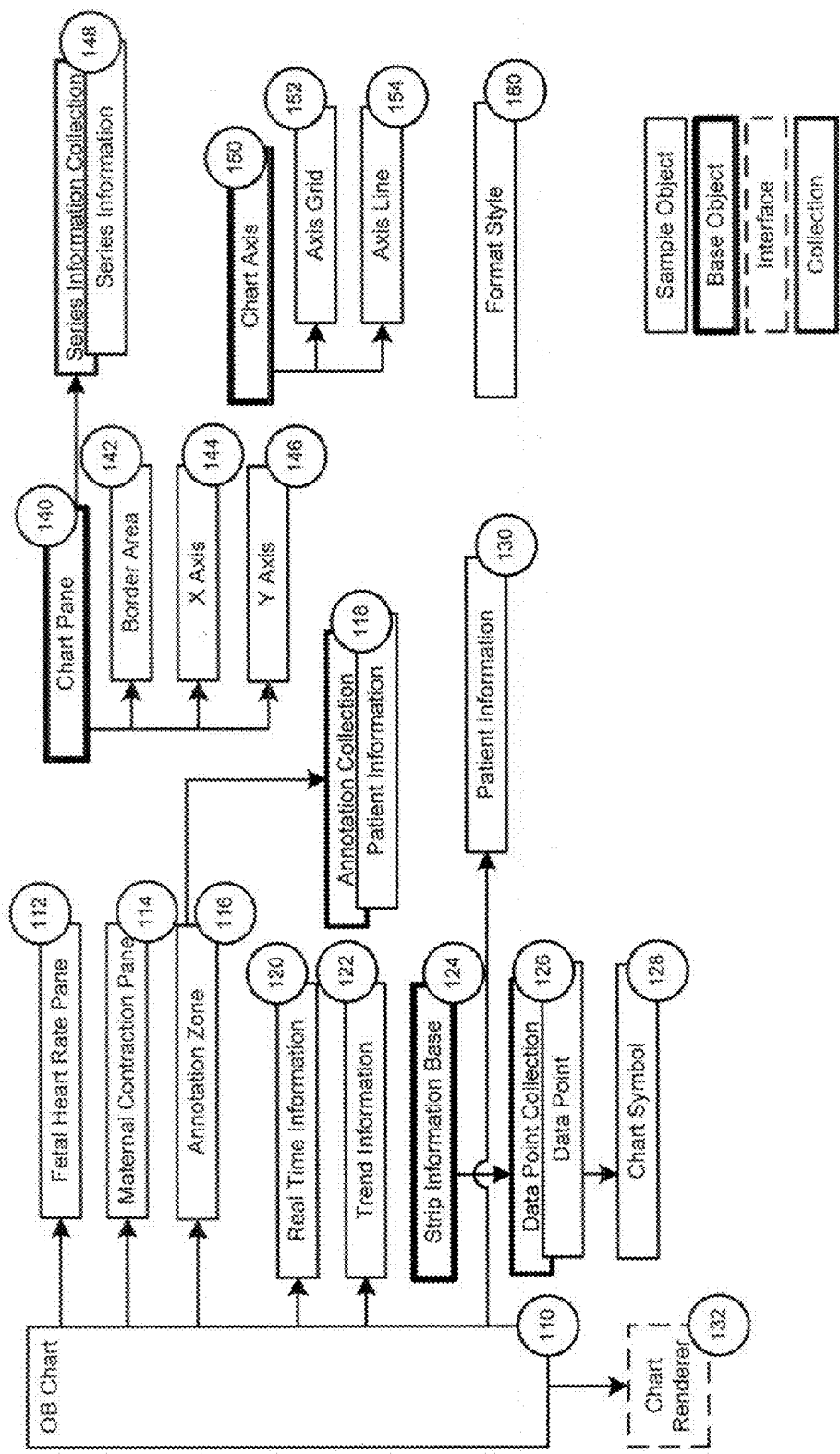
FIG. 3 is a high-level schematic block diagram showing the software architecture for the operation of the system of the present invention, and is a distillation of the object model structure that follows in FIGS. 4A-4D.

As mentioned above, the capabilities of the system of the present invention are established within the proprietary software applications operable within the data collector/database systems within the hospital facilities and the remote wireless handheld devices carried by the physicians. FIG. 3 provides an overview of the software system structure of the present invention that allows for the relatively complex data associated with healthcare monitoring systems to be transmitted, received, and displayed on relatively small and functionally simple handheld devices. FIG. 3 represents a high level summary of the object model of the software system of the present invention and identifies the various objects that are defined, passed, and characterized in the operation of the system.

The fundamental object component of the system is OB Chart Sample Object 110 which, as seen in the diagram, relates to the balance of the object model components in the system. These include the Fetal Heart Rate Pane 112 and Maternal Contraction Pane 114 both of which are sample objects that relate to base object Chart Pane 140. Chart Pane 140 primarily defines Series Information Collection 148, but also defines Border Area 142, X-Axis 144 and Y-Axis 146. X-Axis 144 and Y-Axis 146 relate to base object Chart Axis 150 which includes definitions for Axis Grid 152 and Axis Line 154.

OB Chart sample object 110 also characterizes Annotation Zone 116 which itself defines Annotation Collection 118. OB Chart 110 further relates to Real Time Information sample object 120 as well as Trend Information sample object 122. The Strip Information base object 124 defines the Data Point Collection 126 which itself incorporates Chart Symbol sample object 128. Ancillary Patient Information sample object 130 also is associated with OB Chart 110.

Chart Renderer Interface 132 is associated with OB Chart 110 for the purpose of providing the graphical interface for the information collected. Format Style sample object 160 provides the balance of the display characteristics associated with the information being provided at the remote wireless device. A legend distinguishing the representations of a Sample Object, a Base Object, an Interface, and a Collection is also provided in FIG. 3.

Figure 4A:
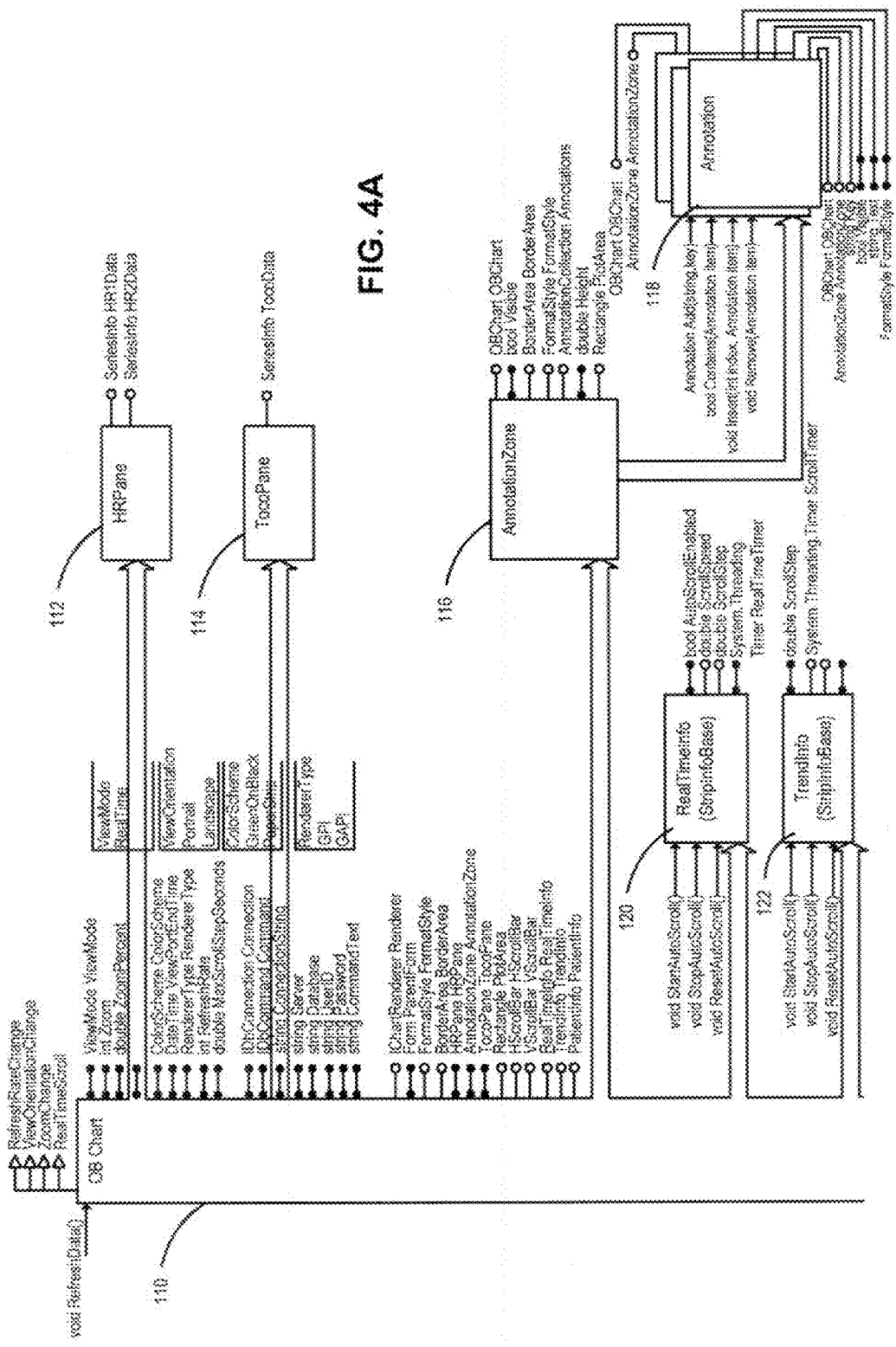
FIGS. 4A-4E provide a series of object model architecture diagrams that describe in greater detail the functionality of the system more generically described in FIG. 3.

The full details of the object model software system of the present invention shown and described in summary form in FIG. 3, are set forth in FIGS. 4A-4E. The various object components, parameters, variables, characteristics, methods, events, and properties associated with each of these objects are set forth. FIG. 4A shows in detail the characteristics and functionality of OBChart object 110 and its connection to HRPane object 112 and TocoPane object 114. Likewise, AnnotationZone object 116 and Annotation Collection 118 relate back to OBChart object 110 as shown. Finally in FIG. 4A, RealTimeInfo (StripInfoBase) object 120 and TrendInfo (StripInfoBase) object 122 are shown to relate back to OBChart object 110 and to define StripInfoBase base object 124 (shown in detail in FIG. 4C).

Figure 4B:
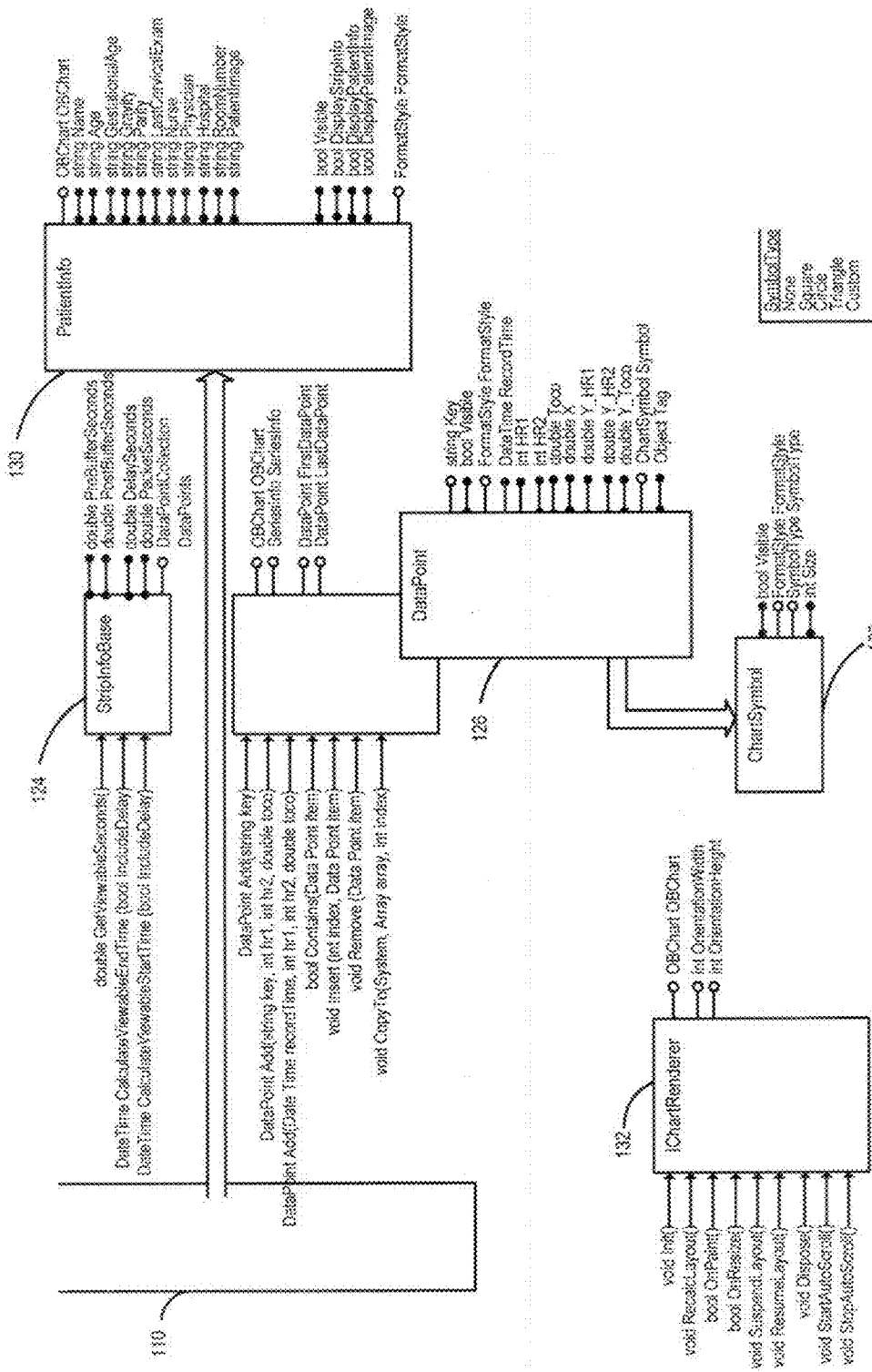

FIG. 4B continues to show the characteristics and functionality of OBChart object 110 and the balance of the display structure directed to the remote wireless handheld device. Base object StripInfoBase 124 derives DataPoint Collection 126 which in turn relates to ChartSymbol object 128. PatientInfo object 130 also operates from OBChart object 110 as shown. Finally in FIG. 4B, IChartRenderer interface 132 operates from OBChart object 110 as shown.

Figure 4C:
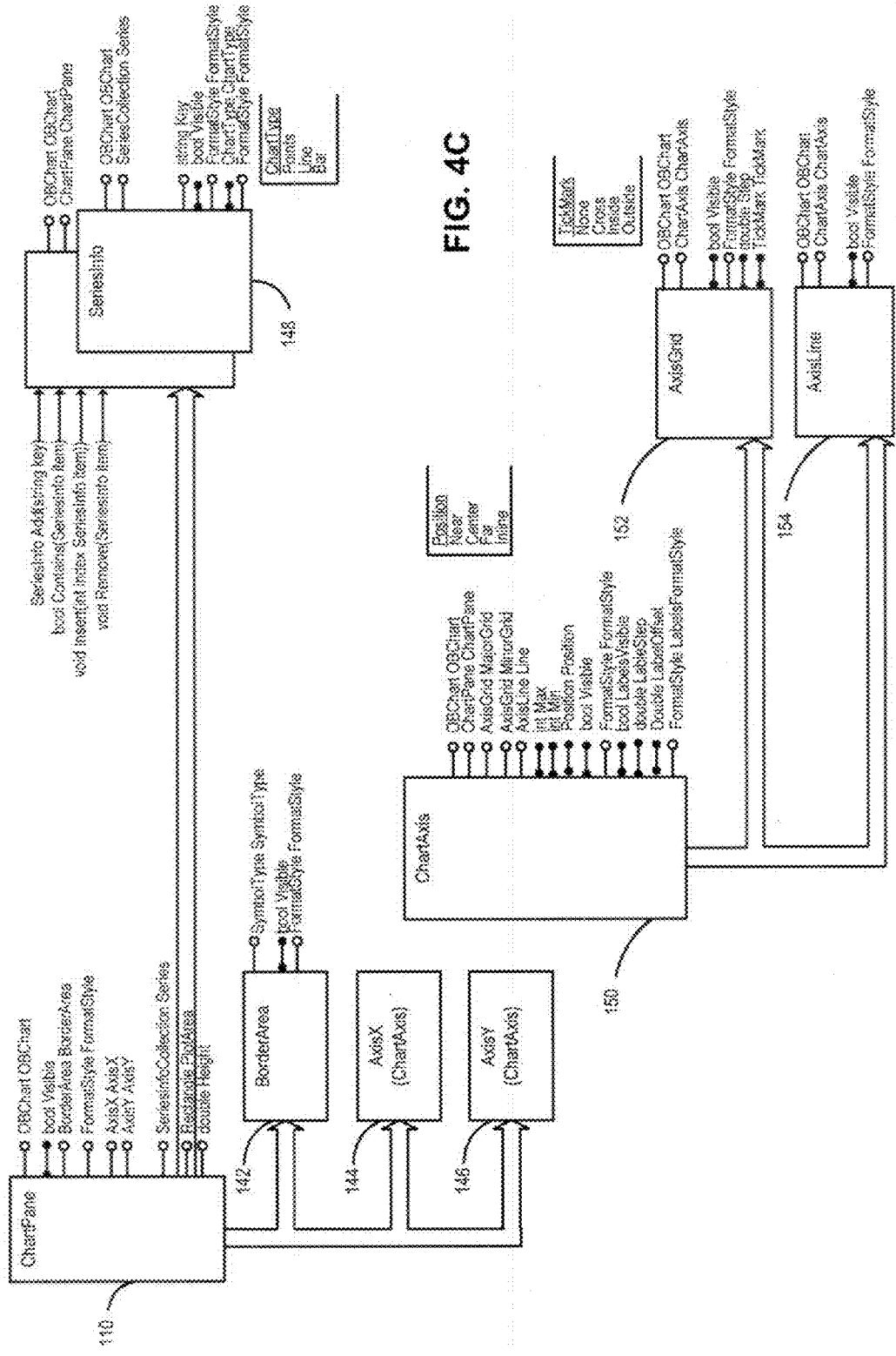

FIG. 4C discloses in detail the structures of base objects ChartPane 140 and ChartAxis 150. ChartPane 140 defines BorderArea object 142, AxisX (ChartAxis) object 144, and AxisY (ChartAxis) 146. AxisX (ChartAxis) object 144 and AxisY (ChartAxis) 146 in turn relate to ChartAxis 150 which defines AxisGrid 152 and AxisLine 154. ChartPane 140 also relates to SeriesInfo Collection 148 as shown.

Figure 4E:
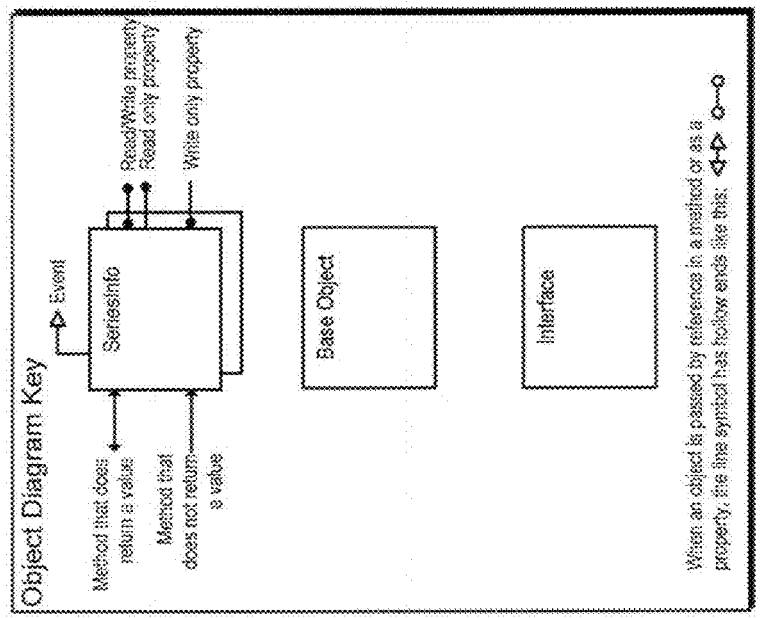
Figure 4D:
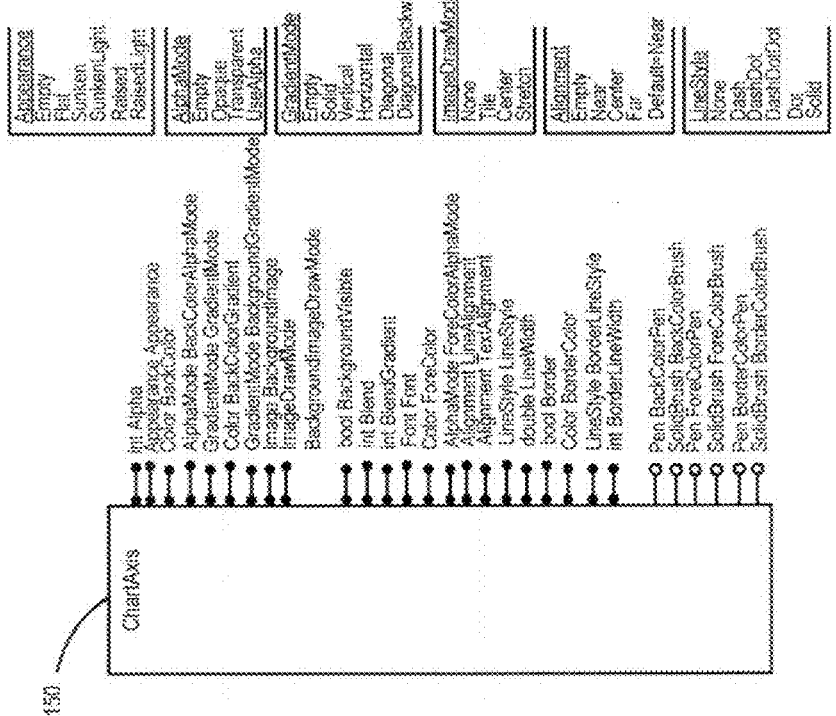

FIG. 4D provides a detailed description of the FormatStyle object 160 which governs the appearance of the display on the remote wireless handheld device. FIG. 4E provides an Object Diagram Key that comprises a legend for the object model diagrams of FIGS. 4A-4D. The key identifies the nomenclature for sample objects, base objects and interfaces. In addition, the key identifies the nomenclature for method connections that return values and those that do not return values, read/write properties and the occurrence of events. Such nomenclature is consistent with the practices in the art of structuring and describing object oriented programming.

Figure 5:
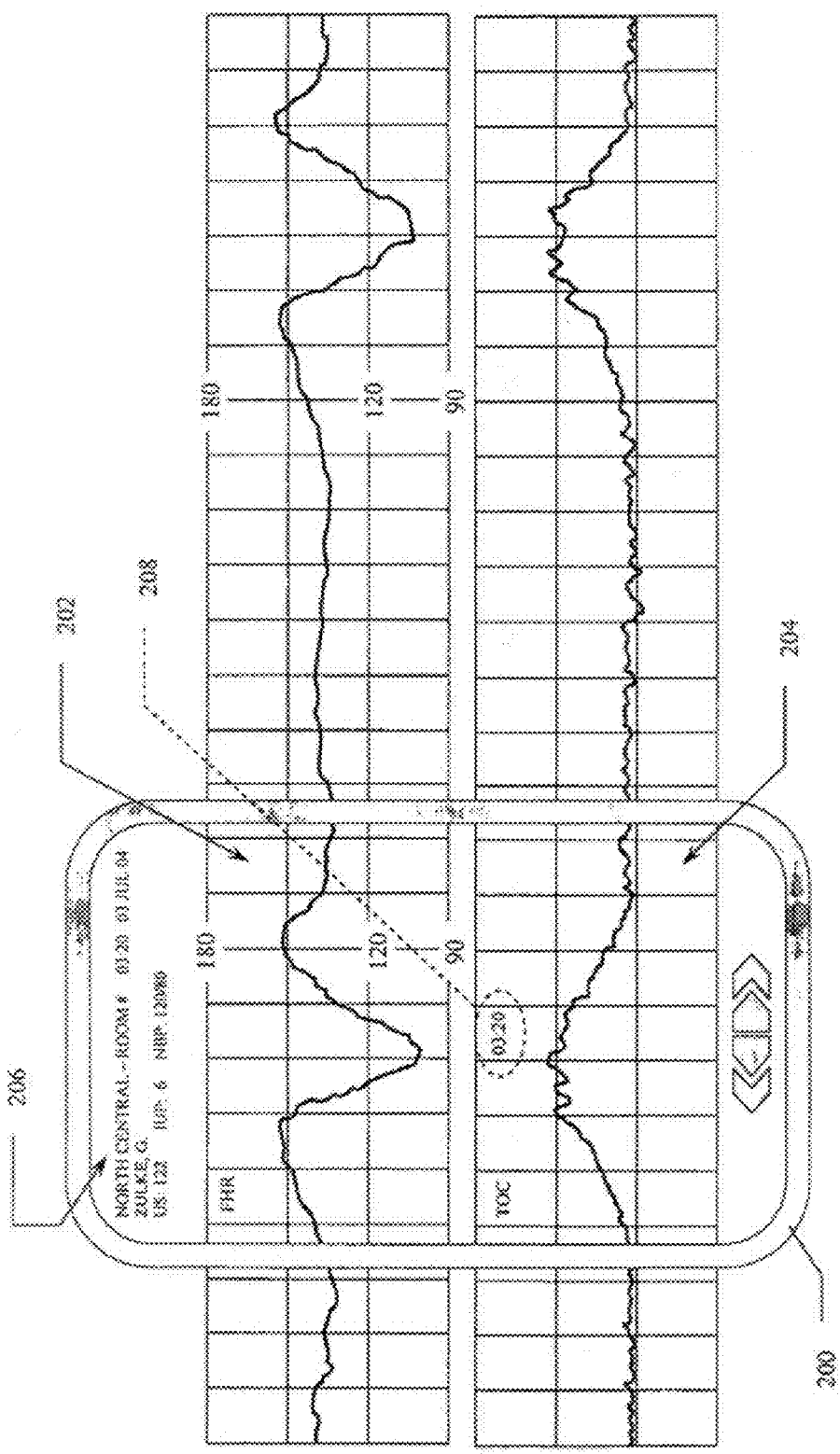
FIG. 5 is a combination diagram showing a representation of a typical handheld device appropriate for use within the system of the present invention and a plot of the two data sets communicated to the display of the handheld device.

Reference is now made to FIG. 5 for an example of the type of information that may be displayed utilizing the systems and methods of the present invention. In this particular example an OB chart strip is provided to the remote physician in sufficiently clear detail to allow the physician to make decisions and recommendations regarding a course of action with the patient. In this diagram a first chart strip 202 showing fetal heart rate is presented above a second chart strip 204 showing maternal contractions (tocometry). A section of the dual strip display is provided at a given moment on the wireless handheld device 200 of the physician. As discussed above, the information streamed (with appropriate buffering) to the wireless device allows for a real time view of the data for purposes of comparison and analysis and a trend view of the data whereby the physician may recall past data received to identify and characterize trends. The typical wireless device configured to receive the data associated with the present invention will have screen controls integrated into the hardwire of the device or presented on the screen of the device itself that will permit the physician to move back and forth across the received data to identify trends. In the example shown on FIG. 5 a characteristic association can be seen between a maternal contraction and significant changes in the fetal heart rate. It is just such a characteristic association that the physician may be able to identify and characterize so as to provide a manner of discerning a course of action for the patient even from the remote location.

Also seen in the display shown in FIG. 5 is the minimal textual information 206 provided on the screen while the graphical data is being displayed. This information 206 may, in the preferred embodiment, contain location and biographical information about the patient sufficient for the physician to know at all times the individual patient associated with the physiological data being viewed. The display would also provide a clear indication of the timing of the information as with time mark 208 to make clear whether the physician is reviewing real-time information of recalling trend information. The time mark 208 may always be compared with the actual time shown on the text display 206.

Figure 6B:
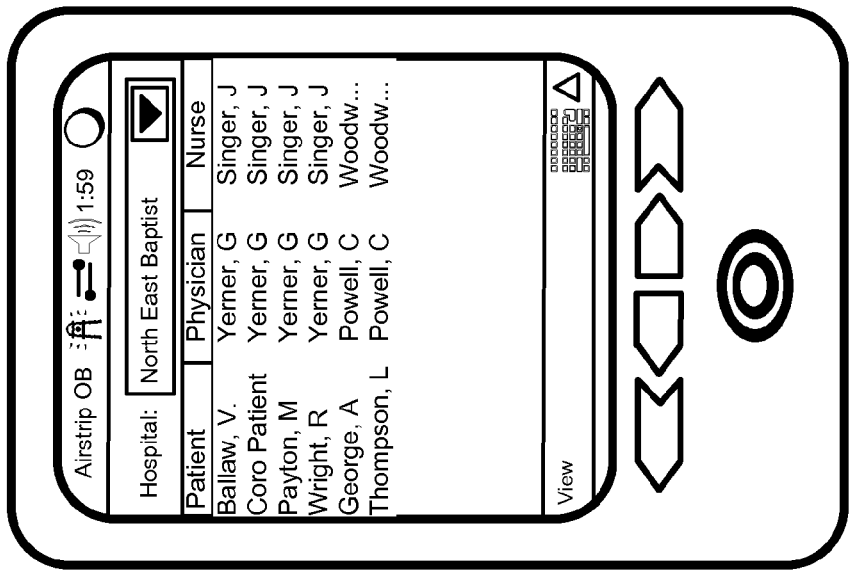
FIGS. 6A-6K are screen-shot images of a display associated with a typical handheld device appropriate for use within the system of the present invention showing the various functional capabilities of the system in providing a versatile display of the patient data.
Figure 6A:
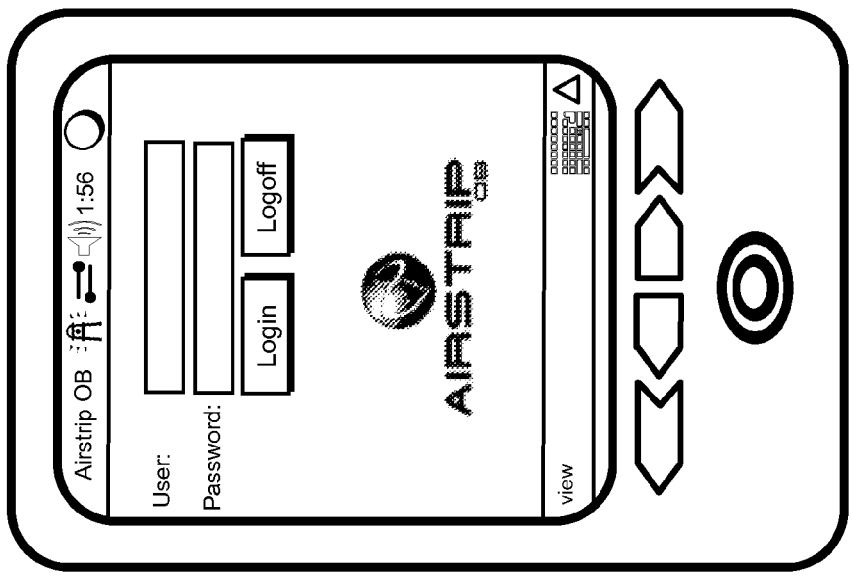

Reference is now made to FIGS. 6A-6K for additional detail on the display features of the present invention as well as the functionality of the hand held device. FIG. 6A discloses a HIPAA compliant login screen that serves to protect the patient information and restrict it to the appropriate physician. The physician would enter a user name and password as is typical in the art. FIG. 6B discloses a display screen that allows the physician to select the facility of concern and the patient of concern. This display is populated with all of the hospitals that the physician is associated with and under each hospital, all of the patients that the physician is responsible for at that hospital.

Figure 6D:
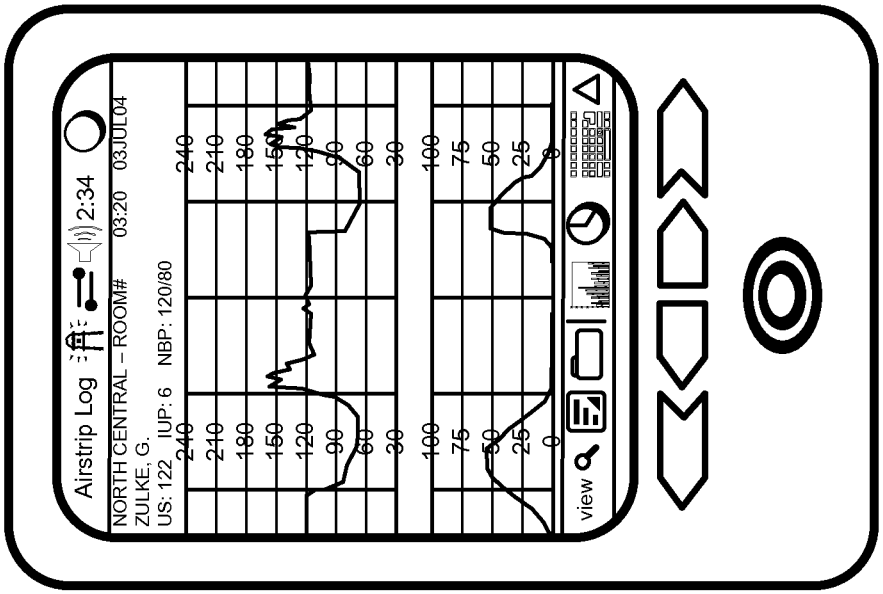
Figure 6C:
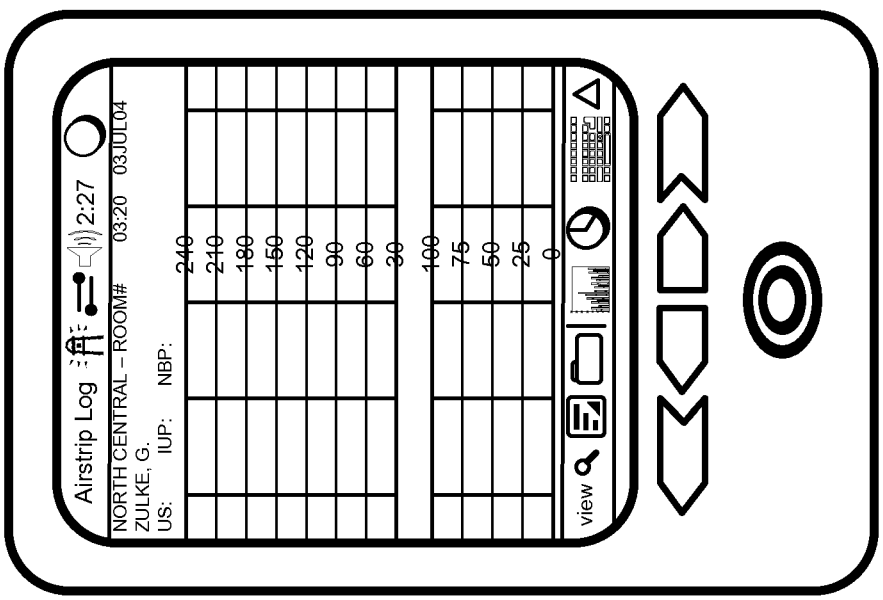

Once the physician selects the hospital and patient of concern the data buffering screen of FIG. 6C is presented providing the background graphic coordinate system and a buffering process alert while the system downloads the data. As can be seen from the programming structure described above, a request is made from the handheld to the hospital server to transmit the data for a specific patient. This information is then transmitted with the handheld device buffering the data to allow for real-time viewing and trend viewing. Typically the system would take about 7 seconds to download up to 4 hours of data.

FIG. 6D provides the basic real-time viewing display wherein the data for a particular patient is presented on the background gird with the timing mark shown and the biographical information on the patient shown. In the preferred embodiment the tracing would move from right to left across the screen in a manner that mimics the view typically seen on instrumentation located onsite in the health care facility.

Figure 6F:
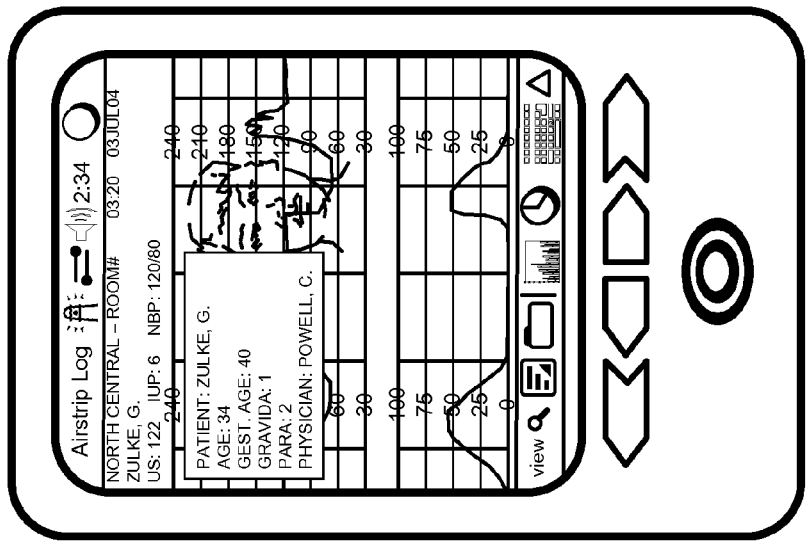
Figure 6E:
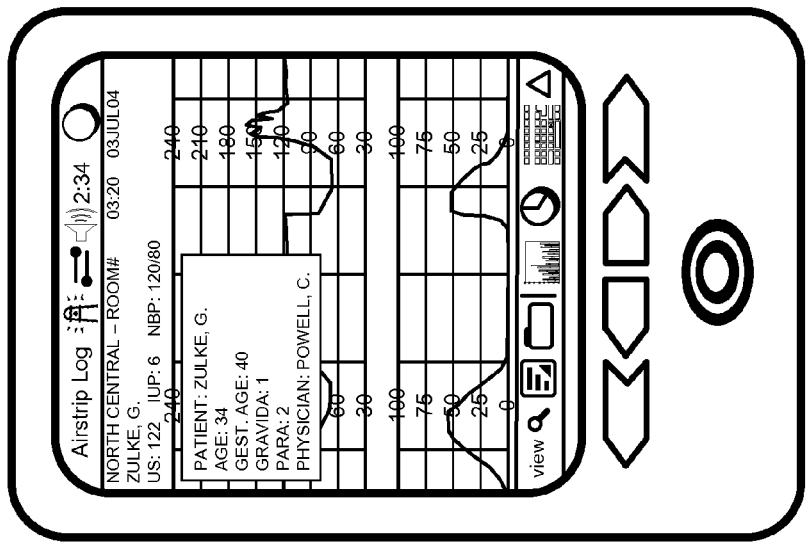

FIG. 6E provides a screen shot of the semi-transparent data overlay window of the present invention that displays information about the patient data being displayed and the manner of the data acquisition (the sensor characteristics, timing, etc.). With this functionality the physician may confirm or verify the environment within which the patient data was acquired and is being presented.

FIG. 6F provides a screen shot of an additional semi-transparent window that displays an image of the patient for recognition purposes. Both the patient image window and the informational window are transparent enough to allow discernment of the trace data displayed beneath them.

Figure 6H:
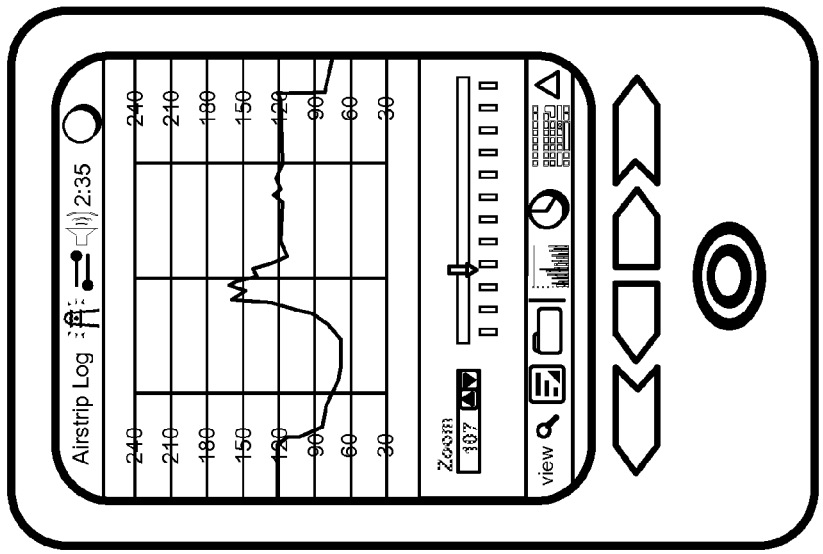
Figure 6G:
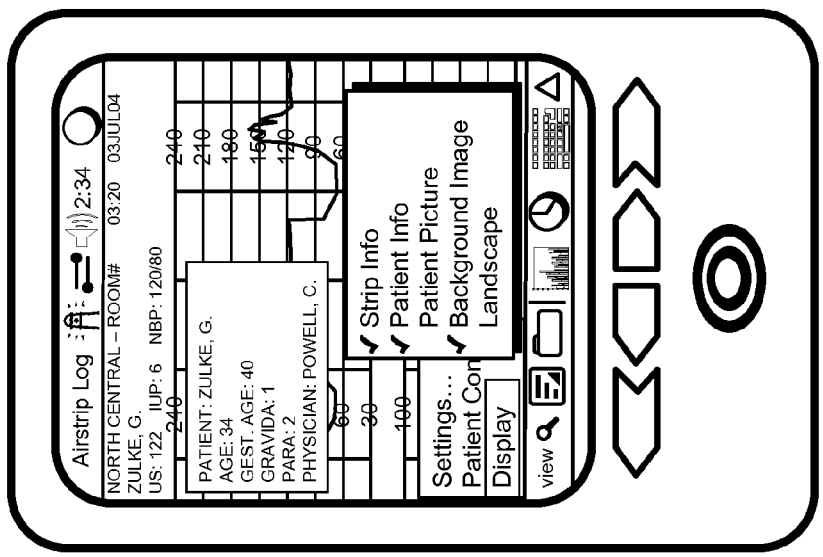

FIG. 6G provides a screen shot of pull-up or pull-down toolbar or menu that allows the physician to select the composition of the display. In addition to the background image, the physician may choose to display the patient information (FIG. 6E), the patient picture (FIG. 6F), and/or the data strip information (FIG. 6D). The physician may also choose to have the display switch to a landscape viewing orientation (described in more detail below).

Figure 6J:
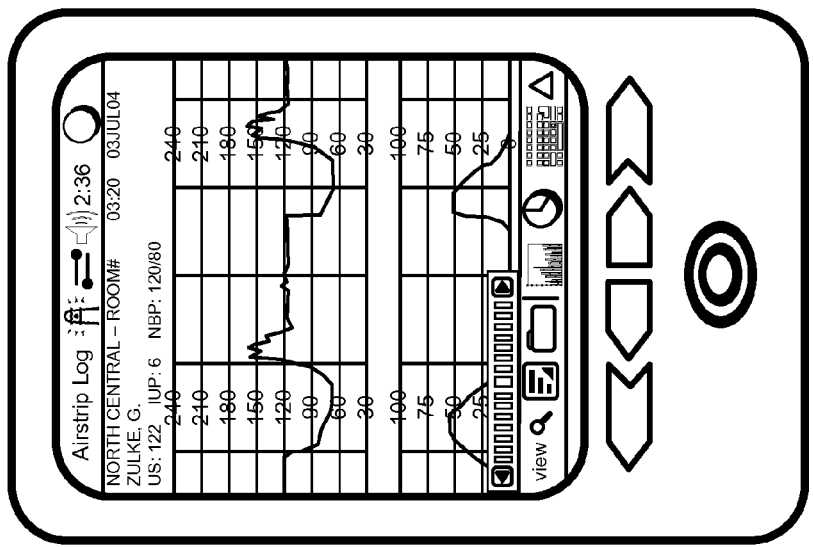
Figure 6I:
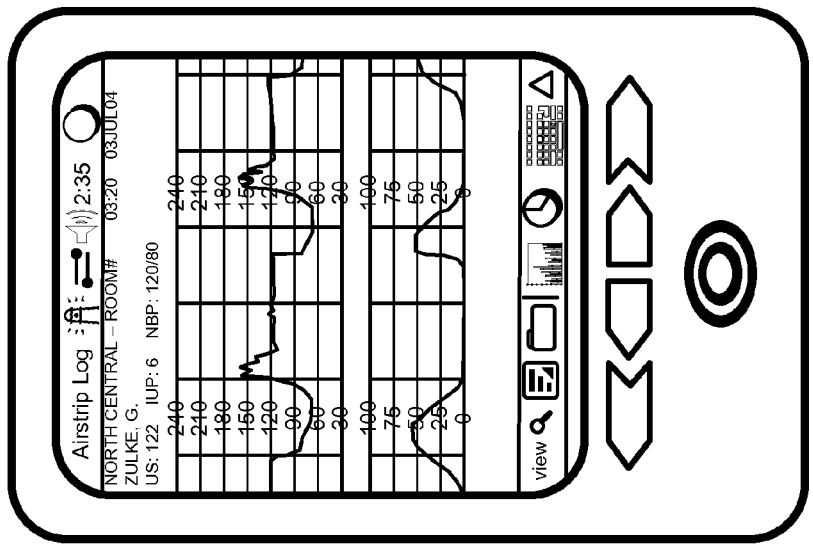

FIGS. 6H & 6I provide screen shots that show the zoom in/out functionality of the system of the present invention (again reference the detailed object model structure of the programming discussed above). In each case (zoom in or zoom out) the physician make take advantage of viewing a trend (zoom out) or a specific data feature (zoom in) to facilitate a judgment with regard to the condition of the patient.

FIG. 6J provides a screen shot of the variable speed scroll functionality of the data display of the present invention. In this view the physician is presented with a bi-directional, multilevel selection bar that controls the direction and the scrolling speed for the data being presented on the display grid. In this manner the physician may customize the viewing of the patient data to personal preferences or to the specific situation that dictated the review of the data. With as much as 4 hours of data available within a download of information, the physician may wish to quickly scroll through the data to a point where anomalies occur and then slow the scrolling down to study the data in more detail. This feature of the present invention permits this modification of the scrolling to occur at the physician's direction.

Figure 6K:
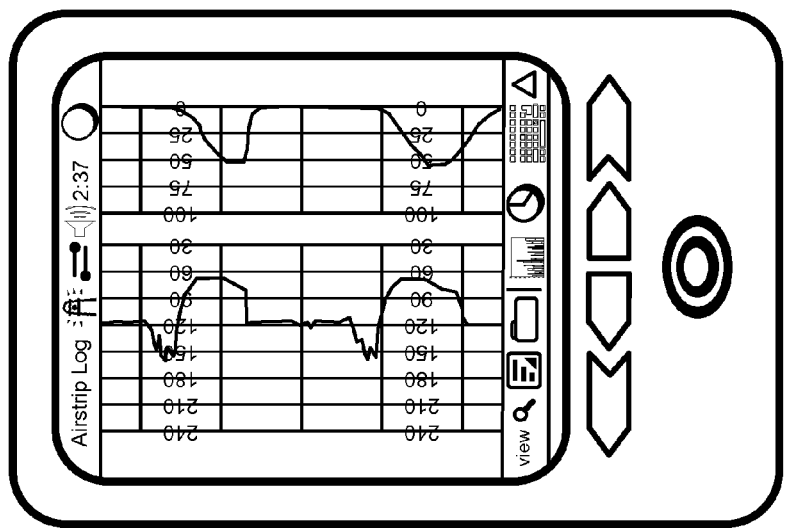

Finally, FIG. 6K provides a screen shot of the data similar to that shown in FIG. 6D but in a landscape presentation on the hand held device display. In this manner the physician may view either a greater amount of data (over a longer time period) in the display, or may view the data set in expanded detail (across the time variable).

The system and method of the present invention as described in the above Detailed Description of the Preferred Embodiments and in the detailed Object Model Structural diagram of the drawing figures, lend themselves to certain modifications that will be apparent to those skilled in the art, which modifications still fall within the scope of the invention. A variety of handheld devices utilizing a number of different operating systems, could implement the system functionality of the present invention. Likewise, the system is not limited to the example given of an OB chart (FHR and Toco) in that a variety of other patient physiological characteristics could be displayed in the same or similar manner. Those skilled in the art will recognize other combinations of data that would be useful to physicians who might be called upon to make patient decisions from locations remote to the patient.

In some aspects, the present disclosure provides a system for the remote monitoring of patient physiological data acquired from at least one patient sensor, said patient physiological data capable of being plotted graphically versus time, the system comprising: (a) a sensor data collection system for collecting said patient physiological data; (b) a healthcare facility data processing and data storage system serving to process and store said patient physiological data; (c) a first graphical data interface (GDI) system operating in conjunction with said healthcare facility data processing and data storage system, said first GDI system for conditioning said patient physiological data for transmittal across a wide area network and for reception and display on a remote data processing device; (d) a remote data processing device operable for the reception and display of said patient physiological data received from said wide area network; and (e) a second graphical data interface (GDI) system operating in conjunction with said remote data processing device, said second GDI for conditioning said patient physiological data for display on said remote data processing device.

In some aspects, said patient physiological data comprises obstetric patient data comprising maternal uterine contraction data and fetal heart rate data.

In some aspects, said patient physiological data comprises cardiopulmonary patient data comprising respiration rate data and heart rate data.

In some aspects, said remote data processing device comprises a wireless device for wireless connection to said wide area network.

In some aspects, remote data processing device comprises a docking device for wired connection to said wide area network.

In some aspects, said remote data processing device comprises a personal data assistant (PDA) having a display screen.

In some aspects, said remote data processing device comprises a smart phone communications device having a display screen.

In some aspects, said remote data processing device comprises a personal computer (PC) having a display screen.

In some aspects, said wide area network comprises the publicly accessible Internet.

In some aspects, said wide area network comprises a privately accessible wired computer network.

In some aspects, said first graphical data interface conditions said patient physiological data by compressing said data.

In some aspects, said first graphical data interface conditions said patient physiological data by identifying and selecting anomalous events within the data.

In other aspects, the present disclosure provides a method for the remote monitoring of patient physiological data acquired from at least one patient sensor, said patient physiological data capable of being plotted graphically versus time, the method comprising the steps of: (a) collecting said patient physiological data from the patient through said at least one patient sensor; (b) processing said patient physiological data so as to make said data amenable to storage on a digital storage device; (c) storing said patient physiological data on said digital storage device; (d) conditioning said patient physiological data for ease of transmission over a wide area digital network; (e) transmitting said patient physiological data over said wide area digital network; (f) receiving said conditioned patient physiological data from said wide area digital network with a remote data processing device, said remote data processing device having a display; (g) reconditioning said received patient physiological data for ease of display on said remote data processing device; and (h) displaying said reconditioned patient physiological data on the display of said remote data processing device.

In some aspects, said patient physiological data comprises obstetric patient data comprising maternal uterine contraction data and fetal heart rate data.

In some aspects, said patient physiological data comprises cardiopulmonary patient data comprising respiration rate data and heart rate data.

In some aspects, said step of conditioning said patient physiological data comprises compressing said data for ease of transmission over said wide area network.

In some aspects, said step of conditioning said patient physiological data comprises identifying and selecting anomalous events within the data.

In some aspects, said step of receiving said conditioned patient physiological data comprises establishing a wireless data communication link with said wide area network and downloading said patient physiological data from said wide area network through said wireless data communication link.

In some aspects, said step of receiving said conditioned patient physiological data comprises establishing a wired data communication link between said remote data processing device and said wide area network and downloading said patient physiological data from said wide area network through said wired data communication link to said remote data processing device.

In some aspects, said step of reconditioning said received patient physiological data comprises formatting said data for display on said remote data processing device, said formatting step providing a reduction in a volume of said data and a reduction in a period of time required to render said data on the display of said data processing device.

In some aspects, said step of displaying said reconditioned patient physiological data comprises time sequentially displaying said data.

In some aspects, said time sequential display of said data comprises a real-time display of said data.

In some aspects, said time sequential display of said data comprises a historical trending time display of said data.

In some aspects, said time sequential display comprises a dynamic progressive display of said data across the display screen of said remote data processing device.

In some aspects, the method further includes the step of controlling the display of said data to alternately present said data in real-time and in historical time, wherein said display may be scrolled across the display screen of said remote data processing device by manipulation of a scrolling control on said device.

In some aspects, the method further includes the step of controlling the display of said data to alternately present said data in portrait orientation and in landscape orientation on the display screen of said remote data processing device.

We claim:

1. A system for the remote monitoring of patient physiological data acquired from at least one patient sensor, said patient physiological data capable of being plotted graphically versus time, the system comprising:
   (a) a sensor data collection system for collecting said patient physiological data;
   (b) a healthcare facility data processing and data storage system operable to (i) process and store said patient physiological data, wherein the processing includes generating multi-channel patient physiological data from the collected patient physiological data (ii) process and store clinical information system (CIS) data collected from external repositories and provide the physiological data and the CIS data to external repositories and devices, and (iii) provide an IT management console for monitoring exchanges of data between external repositories and devices and said healthcare facility data processing and storage system;
   (c) a first graphical application program interface (API) system configured to operate in conjunction with said healthcare facility data processing and data storage system, said first graphical API for conditioning said patient physiological data for streaming across a cellular network and for reception and display on a handheld data processing device by compressing said data;
   (d) a handheld data processing device operable for the reception and display of said multi-channel patient physiological data received from said cellular network, the display of multi-channel patient physiological data comprising simultaneously displaying two or more unique data sets for one patient in real-time, one data set configured for display in a software-generated semi-transparent overlay such that each data set is legibly viewable, and wherein the patient physiological data is displayed in real-time when the handheld data processing device is online and the patient physiological data is cached for future display when the handheld data processing device is offline; and
   (e) a second graphical API system operating in conjunction with said handheld data processing device, said second graphical API system operable to condition said patient physiological data for display on said remote data processing device by formatting said data to optimize data presentation for reduced size presentation of said data on said display screen in said handheld data processing device, said formatting step providing a reduction in a volume of said data and a reduction in a period of time required to render said data on the display of said handheld data processing device,
   wherein said handheld data processing device is configured to buffer said data and display a real-time section of said data as the real-time portion is streamed and a historical section of said data stored in said buffer, wherein a displayed section of said data is collected over a smaller period of time than all of the data stored in the buffer.

2. The system of claim 1 wherein said patient physiological data comprises obstetric patient data comprising maternal uterine contraction data and fetal heart rate data.

3. The system of claim 1 wherein said patient physiological data comprises cardiopulmonary patient data comprising respiration rate data and heart rate data.

4. The system of claim 1 wherein said handheld data processing device comprises a docking device for wired connection to said first graphical API.

5. The system of claim 4 wherein said handheld data processing device comprises a smart phone communications device having a display screen.

6. The system of claim 1 wherein said cellular network is connected to the first graphical API via a privately accessible wired computer network.

7. The system of claim 1 wherein said first graphical API conditions said patient physiological data by identifying and selecting anomalous events within the data.

8. A method for the remote monitoring of patient physiological data acquired from at least one patient sensor, said patient physiological data capable of being plotted graphically versus time, the method comprising the steps of:
   (a) collecting said patient physiological data from the patient through said at least one patient sensor;
   (b) processing said patient physiological data so as to make said data digital for storage on a digital storage device;
   (c) storing said patient physiological data on said digital storage device;
   (d) conditioning said patient physiological data for ease of transmission over a wireless network by compressing said data;
   (e) transmitting said patient physiological data over said wide area digital network;
   (f) receiving said conditioned patient physiological data from said wide area digital network with a remote-handheld data processing device, said remote-handheld data processing device having a display for displaying said patient physiological data in said display or in a software-generated semi-transparent overlay within said display;
   (g) reconditioning said received patient physiological data for ease of display on said remote data processing device, wherein said step of reconditioning said received patient physiological data comprises formatting said data to optimize data presentation for reduced size presentation of said data on said display in said remote data processing device, said formatting step (i) providing a reduction in a volume of said data and a reduction in a period of time required to render said data on the display of said handheld data processing device and (ii) generating multi-channel patient physiological data from said received patient physiological data for simultaneous display in the display screen or in the software-generated semi-transparent overlay within said display; and
   (h) displaying said reconditioned patient physiological data on the display of said remote data processing device.

9. The method of claim 8 wherein said patient physiological data comprises obstetric patient data comprising maternal uterine contraction data and fetal heart rate data.

10. The method of claim 8 wherein said patient physiological data comprises cardiopulmonary patient data comprising respiration rate data and heart rate data.

11. The method of claim 8 wherein said step of conditioning said patient physiological data comprises identifying and selecting anomalous events within the data.

12. The method of claim 8 wherein said step of receiving said conditioned patient physiological data comprises establishing a wired data communication link between said remote-handheld data processing device and said wide area network and downloading said patient physiological data from said wide area network through said wired data communication link to said remote-handheld data processing device.

13. The method of claim 8 wherein said step of displaying said reconditioned patient physiological data comprises time sequentially displaying said data.

14. The method of claim 13 wherein said time sequential display of said data comprises a real-time display of said data.

15. The method of claim 13 wherein said time sequential display of said data comprises a historical trending time display of said data.

16. The method of claim 13 wherein said time sequential display comprises a dynamic progressive display of said data across the display screen of said remote-handheld data processing device.

17. The method of claim 16 further comprising the step of controlling the display of said data to switch the presentation of said data between a real-time presentation and a historical time presentation, wherein said display may be scrolled across the display screen of said remote-handheld data processing device by manipulation of a scrolling control on said device.

18. The system of claim 1, wherein the handheld data processing device is operable to overlay a partially transparent image of the patient on the displayed section of said data, wherein said transparent image is used for recognizing the patient's physical appearance and for verifying an environment within which the patient physiological data was acquired.

19. The system of claim 1, wherein the handheld data processing device operable to display said data in landscape mode and in portrait mode.

20. The system of claim 19, wherein the displayed section of said data corresponds to a longer time period of patient data when the data is displayed in landscape mode than when the data is displayed in portrait mode.

21. The system of claim 1, wherein the second graphical API is configured to operate asynchronously with the first graphical API.

22. The system of claim 1, wherein the handheld data processing device is configured to present screen controls on the screen of the device, and wherein the screen controls are operable to move the displayed section of data backward and forward through the historical section of said data.

* * * * *